United States Patent [19]

Bühler et al.

[11] 4,225,716
[45] Sep. 30, 1980

[54] PROCESS FOR THE MANUFACTURE OF 2,6-DICHLOROPYRIDINE DERIVATIVES

[75] Inventors: Ulrich Bühler, Schöneck; Ernst Heinrich, Neu-Isenburg, both of Fed. Rep. of Germany

[73] Assignee: Cassella Aktiengesellschaft, Frankfurt am Main, Fed. Rep. of Germany

[21] Appl. No.: 7,993

[22] Filed: Jan. 31, 1979

[30] Foreign Application Priority Data

Apr. 3, 1978 [DE] Fed. Rep. of Germany ....... 2814330

[51] Int. Cl.² .................. C07D 213/55; C07D 213/57
[52] U.S. Cl. .................................. 546/286; 546/287; 546/315; 546/326; 546/345
[58] Field of Search ............... 546/345, 315, 326, 286, 546/287

[56] References Cited

U.S. PATENT DOCUMENTS 2,742,478   4/1956   Bavley et al. ...................... 546/345

OTHER PUBLICATIONS

Sawa et al., Chem. Abstracts, vol. 62, No. 10, 11,786a, May 10, 1965.
Bobbitt et al., Journal of Organic Chemistry, vol. 25, No. 3, pp. 560–564, Mar. 1960.

*Primary Examiner*—Alan L. Rotman
*Attorney, Agent, or Firm*—Connolly and Hutz

[57] ABSTRACT

The process for the manufacture of a compound of the formula

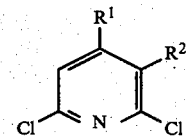

comprising reacting in the presence of a basic nitrogen compound at elevated temperature phosphorus oxychloride with a compound of the formula

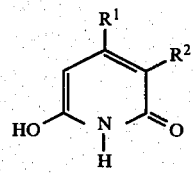

in the molar ratio of phosphorus oxychloride to hydroxypyridine of 1:1 to 1.3:1 wherein
$R^1$ is hydrogen, alkyl having 1 to 8 carbon atoms, phenyl, carbalkoxy having 2 to 5 total carbon atoms, carbalkoxymethyl having 3 to 6 total carbon atoms or substituted phenyl having a substituent selected from the group consisting of chloro, bromo, methyl, ethyl, methoxy, ethoxy, cyano and nitro and $R^2$ is hydrogen, cyano, nitro or acetyl.

5 Claims, No Drawings

PROCESS FOR THE MANUFACTURE OF 2,6-DICHLOROPYRIDINE DERIVATIVES

The invention relates to a process for the manufacture of compounds of the general formula I

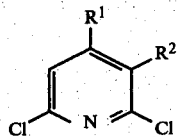

in which $R^1$ denotes hydrogen, alkyl having 1 to 8 C atoms, phenyl which is optionally substituted by chlorine, bromine, methyl, ethyl, methoxy, ethoxy, cyano or nitro, carbalkoxy having a total of 2 to 5 C atoms or carbalkoxymethyl having a total of 3 to 6 C atoms and $R^2$ denotes hydrogen, cyano, nitro or acetyl.

It is known to react 6-hydroxy-3-cyano-4-methylpyrid-2-one or 6-hydroxy-3-cyano-1,4-dimethylpyrid-2-one with phosphorus oxychloride in order to manufacture 2,6-dichloro-3-cyano-4-methylpyridine; compare Bobbitt and Scola, Journ. Org. Chem. 25 (1960), 562 and German application laid open to public inspection 2,049,831. In these processes, however, 3.9 and, respectively, 2.9 mols of phosphorus oxychloride are employed, based on the starting pyridone, and in the case of 6-hydroxy-3-cyano-4-methylpyrid-2-one the reaction must be carried out in an autoclave. It is further known that certain 6-hydroxypyrid-2-ones and the 2,6-dihydroxypyridines tautomeric therewith can be reacted with phosphorus oxychloride, without using excess pressure, to give the corresponding 2,6-dichloropyridines if basic nitrogen compounds, especially tertiary amines, are present and specific molar ratios are maintained; compare Japanese Patent Application Sho No. 39-26850 (C.A. (1965) 62, 11786a), U.S. Pat. No. 2,742,478 and German application laid open to public inspection No. 2,127,521. In these processes, at least a 2-molar excess of phosphorus oxychloride must be employed per 1 mol of starting material, that is to say of the 6-hydroxypyrid-2-one compound.

Surprisingly, it has now been found that when 2,6-dihydroxypyridine compounds are reacted with phosphorus oxychloride in the presence of basic nitrogen compounds a substantial reduction in the amount of phosphorus oxychloride is possible and considerable advantages are thus achieved.

The invention therefore relates to a process for the manufacture of compounds of the general formula I, in which a compound of the general formula II

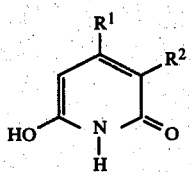

in which $R^1$ and $R^2$ are as defined, is reacted with phosphorus oxychloride in the presence of a basic nitrogen compound at elevated temperature. The process according to the invention is characterised in that the compound of the general formula II and phosphorus oxychloride are used in a molar ratio of 1:(1 to 1.3).

The compound of the general formula II can also be in the tautomeric form, for example in the form of the 2,6-dihydroxypyridine compound.

Based on 1 mol of the starting compound of the general formula II, 0.1 to 1.5 mols, preferably 0.4 to 1.5 mols, of the basic nitrogen compound are usually employed. It is usually not necessary to use more than 1.5 mols of the basic nitrogen compound. Basic nitrogen compounds which can be used are, in particular, tertiary aliphatic or aromatic amines or simple nitrogen heterocyclic compounds, such as, for example, trimethylamine, triethylamine, N-methylpiperidine, N-methylpyrrolidone, pyridine and N,N-dimethyl-m-toluidine. The amines which are insoluble or only slightly soluble in cold water, such as, for example, isoquinoline, carbazole, acridine, 2-methyl-4-ethylpyridine, 2-methyl-5-ethyl-pyridine, 2-methyl-6-ethyl-pyridine, 4-methyl-3-ethyl-pyridine, tri-n-propylamine, tri-n-butylamine and also N,N-dimethylaniline and N,N-diethylaniline, are preferred, especially for reasons of economy and low pollution of the environment. Amines which have moderate solubility in cold water, such as, for example, quinoline, are also preferred if they are steam-volatile. Mixtures of 2 or more basic nitrogen compounds can also be used.

Examples of substituents possible as $R^1$ are: methyl, ethyl, n-propyl, i-propyl, n-butyl, i-butyl, n-hexyl, β-ethylhexyl, carbomethoxy, carboethoxy, carbo-n-propoxy, carbo-n-butoxy, carbomethoxymethyl, carboethoxymethyl and carbobutoxymethyl. Examples of R are: methyl, ethyl, n-propyl, i-propyl, n-butyl, n-hexyl and β-ethylhexyl.

Preferred substituents are methyl, ethyl and n-propyl for $R^1$ and cyano for $R^2$.

Based on 1 mol of the starting compound of the general formula II, 1 to 1.3 mols of phosphorus oxychloride and 0.1 to 1.5 mols of the basic nitrogen compound are mixed with one another and the reaction is carried out at temperatures of 150° to 250° C., preferably 170° to 220° C., appropriately with stirring. Most simply, the reflux temperature of the batch in an open system is chosen as the reaction temperature for the reaction according to the invention. Since the amount of phosphorus oxychloride decreases as the reaction proceeds and the bulk of the basic nitrogen compound is bonded in the form of the hydrochloride, reaction temperatures of up to 250° C. can be reached without applying excess pressure. The reaction times vary between 2 and 5 hours, depending on the reaction temperature.

The reduction, according to the invention, in the amount of phosphorus oxychloride makes possible substantially better utilisation of the chlorinating agent. Furthermore, working up of the reaction batch is simplified by the reduction in the amount of phosphorus oxychloride. Whilst in the case of the processes known hitherto it was necessary, after the reaction, to distil off excess phosphorus oxychloride or carefully to destroy it by adding ice, in which case it passed as phosphate into the effluent, the procedure followed for working up in the case of the process according to the invention is preferably to allow cold or even hot water to run into the hot reaction mixture and, during this addition, appropriately to maintain the reaction mixture at a temperature which is above, preferably 5° to 20° C. above, the melting point of the synthesised 2,6-dichloropyridine compound of the formula I. A finely crystalline product of analytical purity is obtained immediately with this procedure. The use of basic nitrogen compounds which are sparingly soluble in cold water prevents a load on the effluent since these compounds precipitate from the neutralised filtrate of the hydrolysed reaction mixture and can easily be separated off quantitatively. Steam-volatile basic nitrogen compounds can be recovered from the filtrate by steam distillation.

EXAMPLE 1

150 g of 2,6-dihydroxy-3-cyano-4-methyl-pyridine are added to a solution of 65 g of quinoline and 184 g of phosphorus oxychloride, at room temperature. The temperature rises to about 65° C. The reaction mixture is now heated to 190° C. (internal temperature) in the course of 75 minutes, with stirring, and is stirred at this temperature for 3 hours. The batch is then allowed to cool to 125° C. (internal temperature), likewise with stirring, 250 ml of hot water are added dropwise at this temperature and the mixture is stirred cold overnight and filtered. The residue is washed with water until neutral and dried under reduced pressure. This gives 180 g of 2,6-dichloro-3-cyano-4-methyl-pyridine in the form of a colourless powder which without further purification melts at 113° C. and gives the following analytical values:

| Analysis: $C_7H_4N_2Cl_2$ | C | H | N | Cl |
|---|---|---|---|---|
| calculated: | 44.9 | 2.1 | 15.0 | 38.0 |
| found: | 45.0 | 2.1 | 15.0 | 37.7 |

The filtrate is neutralised with sodium hydroxide solution and cooled and the quinoline which has precipitated is separated off. The aqueous phase is subjected to a steam distillation and the quinoline obtained is combined with the bulk of the quinoline already separated off. The quinoline recovered can be used for a new batch.

EXAMPLE 2

129 g of quinoline, 154 g of phosphorus oxychloride and 150 g of 2,6-dihydroxy-3-cyano-4-methyl-pyridine are reacted in the manner described in Example 1.

Yield: 180 g of 2,6-dichloro-3-cyano-4-methylpyridine.

Further dichloropyridine derivatives, which are listed in the table which follows, were prepared analogously to the procedure described:

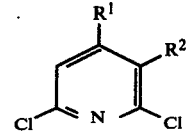

| Example | $R^1$ | $R^2$ |
|---|---|---|
| 3 | $C_2H_5$ | CN |
| 4 | n-$C_3H_7$ | CN |
| 5 | n-$C_4H_9$ | CN |
| 6 | $CH_2CH(CH)_3CH_3$ | CN |
|   | $\vert$ |   |
|   | $CH_3$ |   |
| 7 | $C_6H_5$ | CN |
| 8 | –⟨◯⟩–$OC_2H_5$ | CN |

-continued

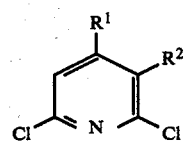

| Example | $R^1$ | $R^2$ |
|---|---|---|
| 9 | –⟨◯⟩–$CH_3$ | CN |
| 10 | –⟨◯⟩–Cl | CN |
| 11 | $CH_2COOCH_3$ | CN |
| 12 | $COOCH_3$ | CN |
| 13 | $COOC_2H_5$ | CN |
| 14 | $CH_3$ | H |
| 15 | H | H |
| 16 | $CH_3$ | $NO_2$ |
| 17 | $C_2H_5$ | $NO_2$ |
| 18 | $CH_3$ | $COCH_3$ |
| 19 | $C_6H_5$ | $COCH_3$ |

The compounds of the general formula I are valuable intermediate products for the manufacture of dyestuffs, especially of coupling components which possess substituted amino groups in the 2- and 6-position.

The starting compounds of the general formula II are known or can be manufactured easily by the processes known for analogous compounds. Such processes are described, for example, in the monograph "Pyridine and its Derivatives, Part one" Chapter II, which was published in 1960 by Interscience Publishers Inc., New York in the series "The Chemistry of Heterocyclic Compounds", edited by Arnold Weissberger. A manufacturing process which is frequently advantageous is that of I. Guareschi, reported in Chemisches Zentralblatt 1896 I., 601 and Berichte der Deutschen Chemischen Gesellschaft 29, R. 654 (1896).

We claim:

1. In the process for the manufacture of a compound of the formula

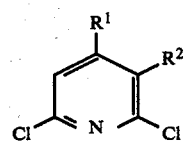

comprising reacting in the presence of a basic nitrogen compound at elevated temperature phosphorus oxychloride with a hydroxypyridine of the formula

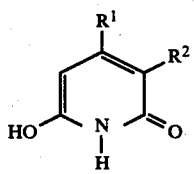

wherein
$R^1$ is hydrogen, alkyl having 1 to 8 carbon atoms, phenyl, carbalkoxy having 2 to 5 total carbon atoms, carbalkoxymethyl having 3 to 6 total carbon atoms or substituted phenyl having a substituent selected from the group consisting of chloro, bromo, methyl, ethyl, methoxy, ethoxy, cyano and nitro and $R^2$ is hydrogen, cyano, nitro or acetyl, the improvement comprises the molar ratio of phosphorus oxychloride to hydroxypyridine being 1:1 to 1.3:1.

2. The process according to claim 1 wherein water is introduced into the reaction batch at the end of the reaction while the latter is still hot.

3. The process according to claim 2, wherein during the introduction of water a temperature is maintained which is above the melting point of the product compound of the formula

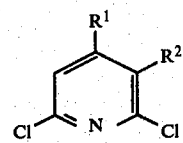

4. The process according to claim 3 wherein during the introduction of water a temperature is maintained which is 5° to 20° C. above the melting point of the product compound.

5. The process according to claim 1 wherein $R^1$ is methyl and $R^2$ is cyano.